United States Patent
Findeis et al.

(10) Patent No.: US 6,216,031 B1
(45) Date of Patent: Apr. 10, 2001

(54) APPARATUS FOR ENHANCING SIGNALS IN ECGS ARTEFACTS

(75) Inventors: Martin Findeis; Willi Kaiser, both of Freiburg i. Br. (DE)

(73) Assignee: Marquette Hellige GmbH, Frieburg I.Br (DE)

( * ) Notice: Subject to any disclaimer, the term of this patent is extended or adjusted under 35 U.S.C. 154(b) by 0 days.

(21) Appl. No.: 09/248,624

(22) Filed: Feb. 11, 1999

(30) Foreign Application Priority Data

Feb. 11, 1998 (DE) .............................. 198 05 530

(51) Int. Cl.⁷ .................................................. A61B 5/0402
(52) U.S. Cl. ............................................. 600/509; 128/901
(58) Field of Search ................................ 600/509, 515, 600/516, 518, 521; 128/901

(56) References Cited

U.S. PATENT DOCUMENTS

| | | | |
|---|---|---|---|
| 5,564,428 | 10/1996 | Soernmo et al. | 128/696 |
| 5,687,735 | 11/1997 | Forbes et al. | 128/696 |
| 5,792,069 | * 8/1998 | Greenwald et al. | 607/45 |

FOREIGN PATENT DOCUMENTS

| | | | |
|---|---|---|---|
| 39 12 028 A1 | 10/1989 | (DE) | G01R/29/00 |
| 1-227740 | 9/1989 | (JP) | A61B/5/04 |

OTHER PUBLICATIONS

J. A. Van Alste, "Removal of Base–Line Wander and Power–Line Interference from the ECG by an Efficient FIR Filter with a Reduced Number of Taps" IEEE Transactions on Biomedical Engineering, vol. BME–32, No. 12, Dec. 1985.

X.G. Yan, "Dynamic Levkov–Christov Subtraction of Mains Interference," Medical & Biological Engineering & Computing, pp. 635–638, Nov. 1993.

* cited by examiner

Primary Examiner—Kennedy Schaetzle
(74) Attorney, Agent, or Firm—Michael, Best et al.; Christian G. Cabou; Phyllis Y. Price

(57) ABSTRACT

The present invention relates to an apparatus for enhancing signals In ECGs including artefacts, said apparatus comprising a mean value unit (4) for evaluating from an ECG signal the curve shape of a predetermined number of beats from the beginning of a QRS complex to the end of a T wave and forming therefrom a mean value beat. A subtracting unit (3) subtracts the mean value beat from the ECG signal of an actual beat to thereby obtain a residual signal. A FIR filter unit (4) subjects the residual signal to high-low-pass filtering and delays it to provide a filtered signal to which the mean value beat is added in an adding unit.

11 Claims, 10 Drawing Sheets

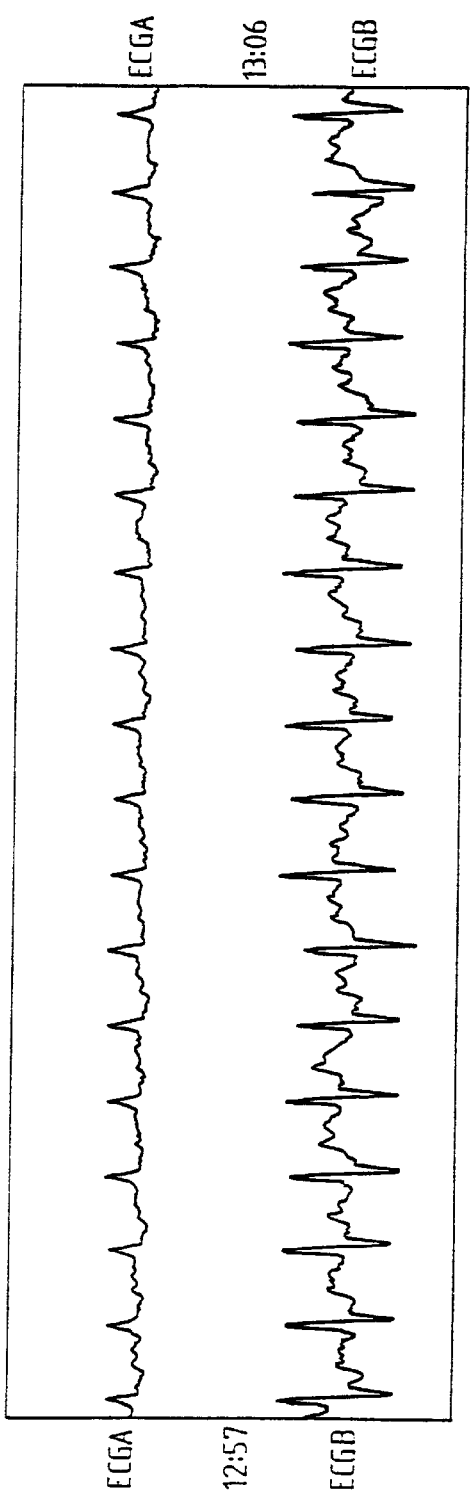
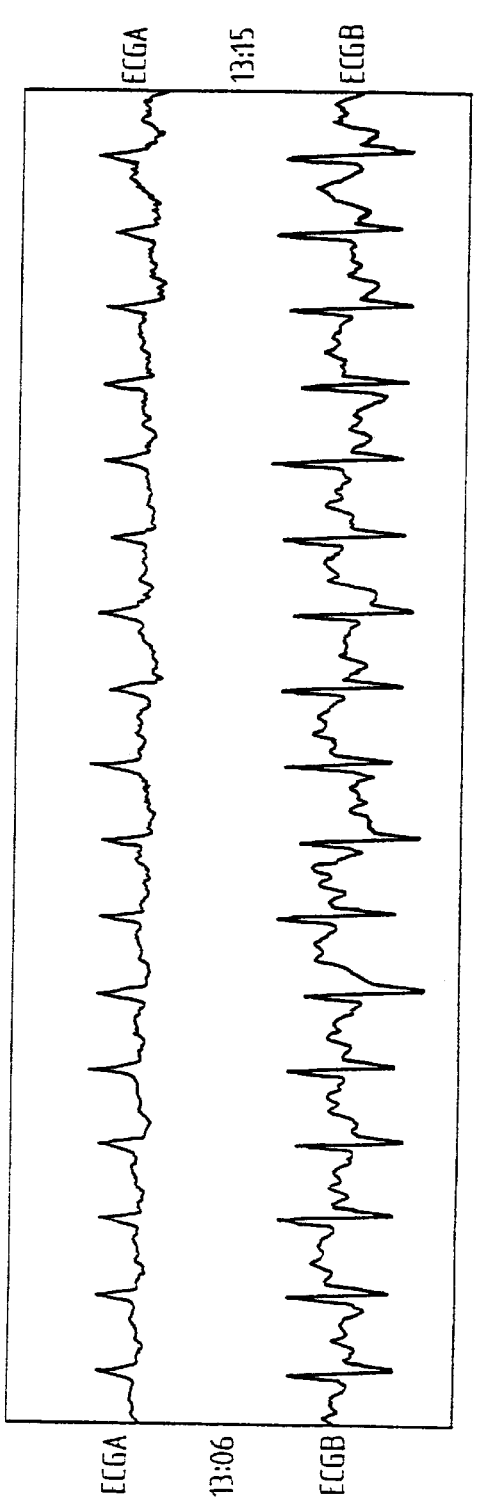
Fig. 3

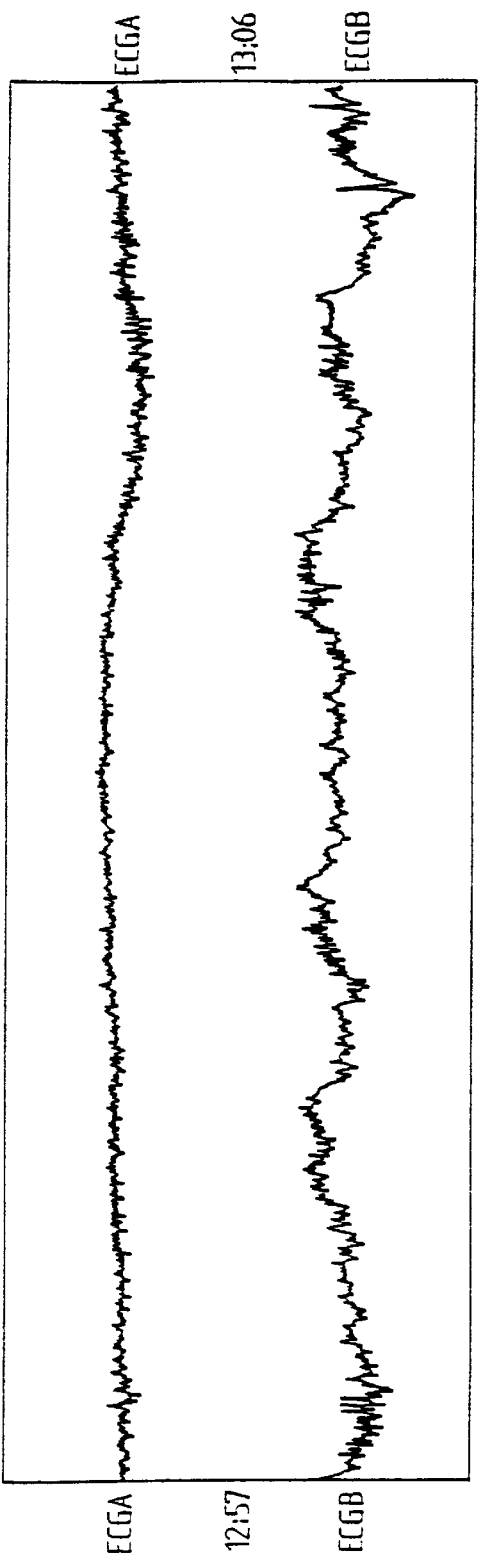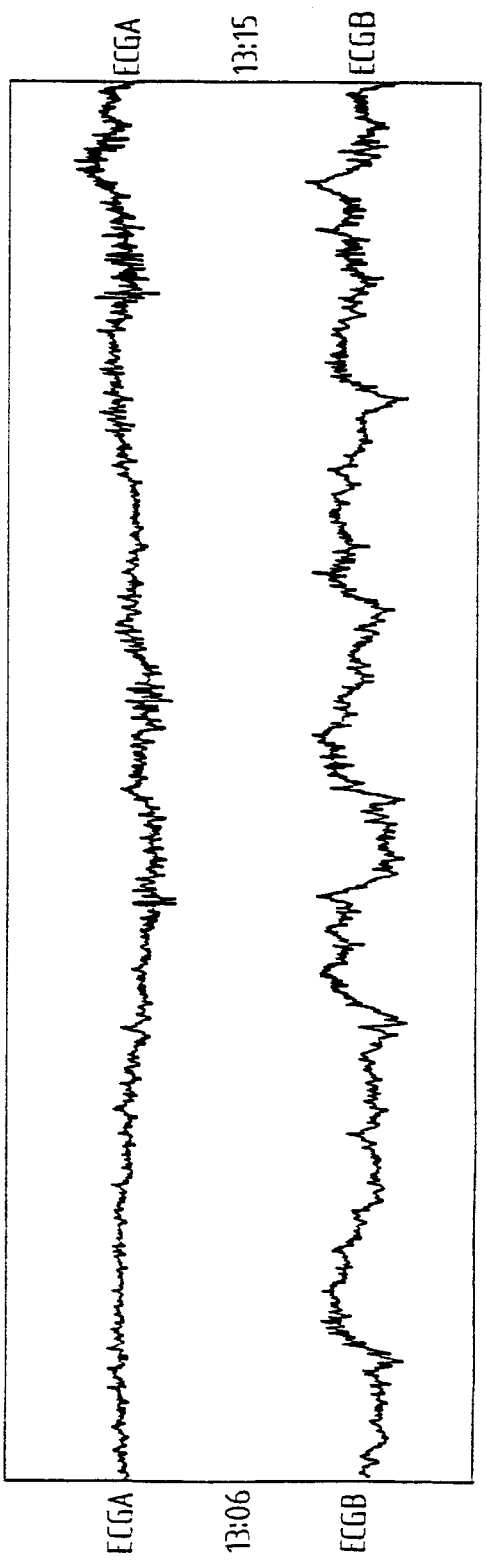
Fig. 5

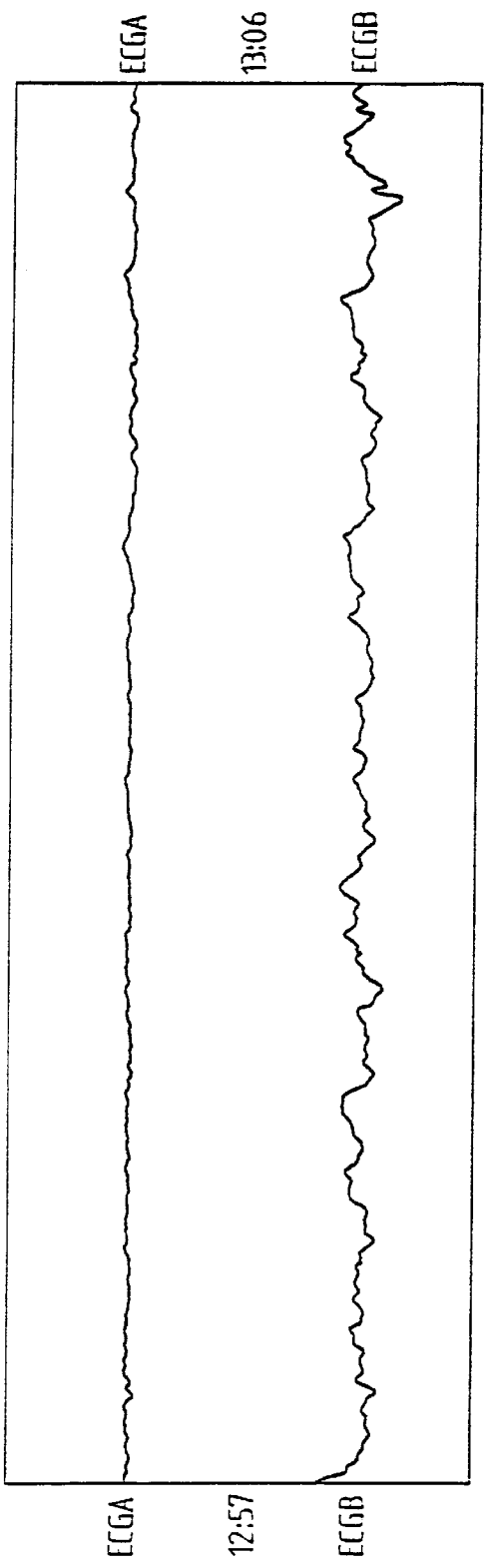
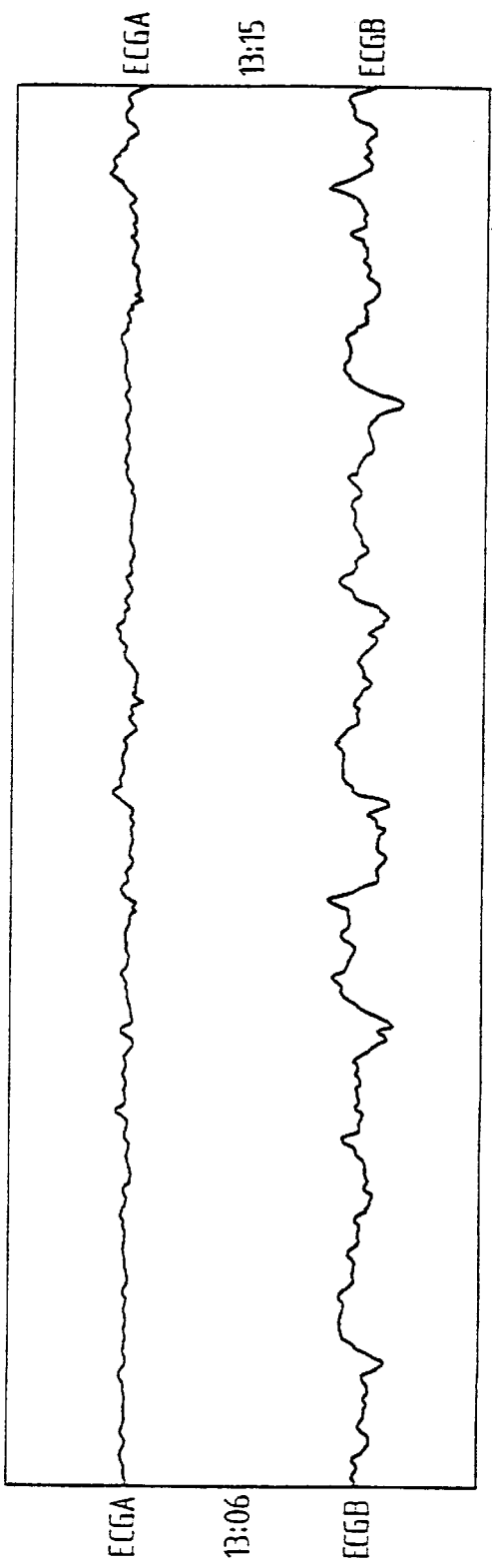
Fig. 8

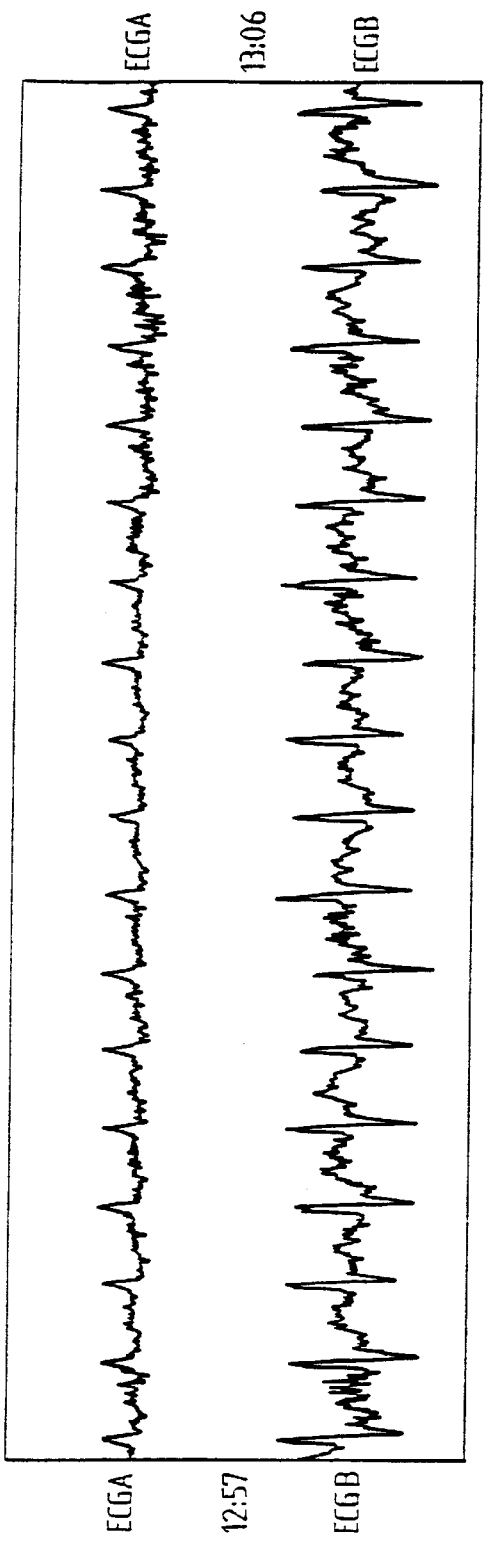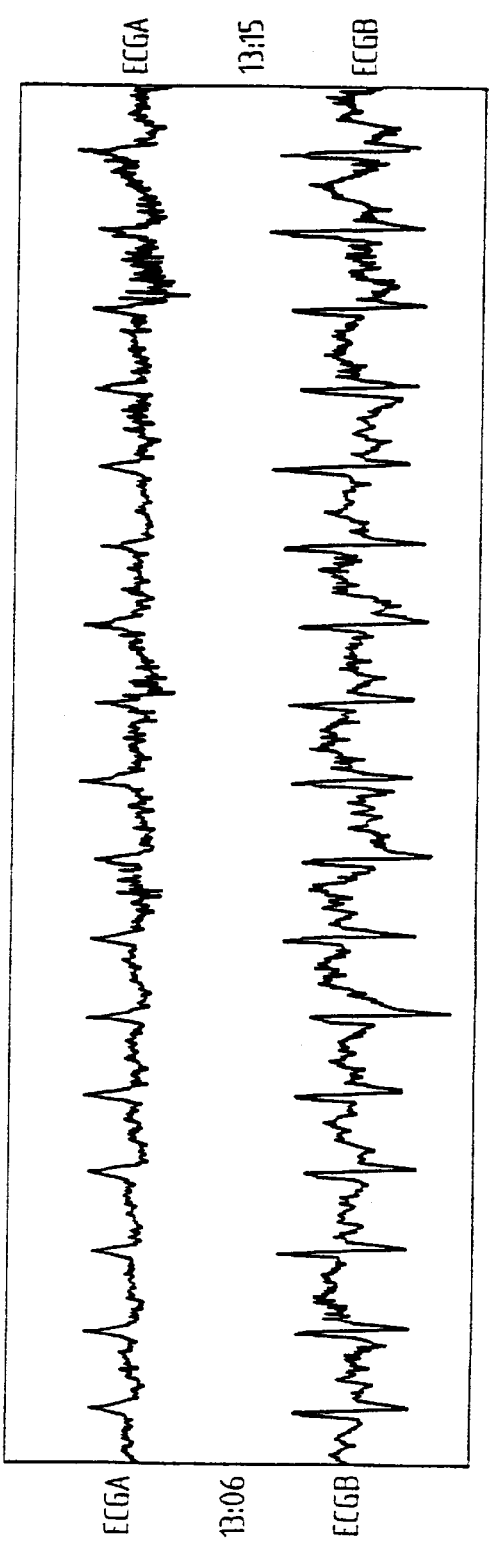
Fig. 9

Fig. 10
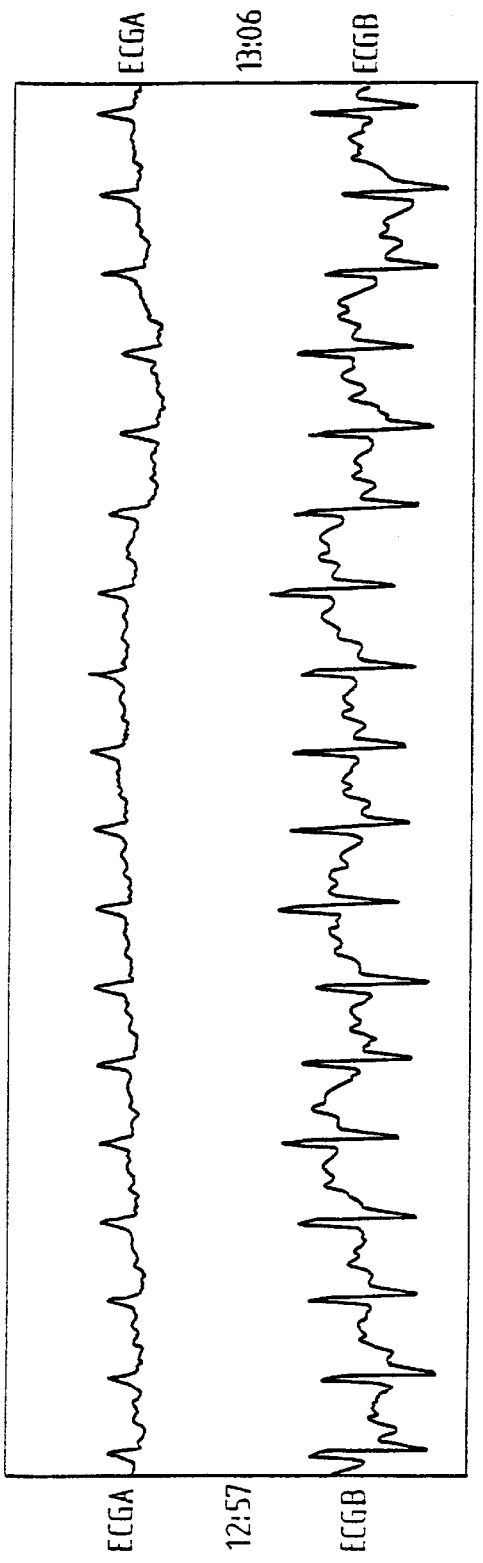
ECG after filtering with FRF without high-pass filter
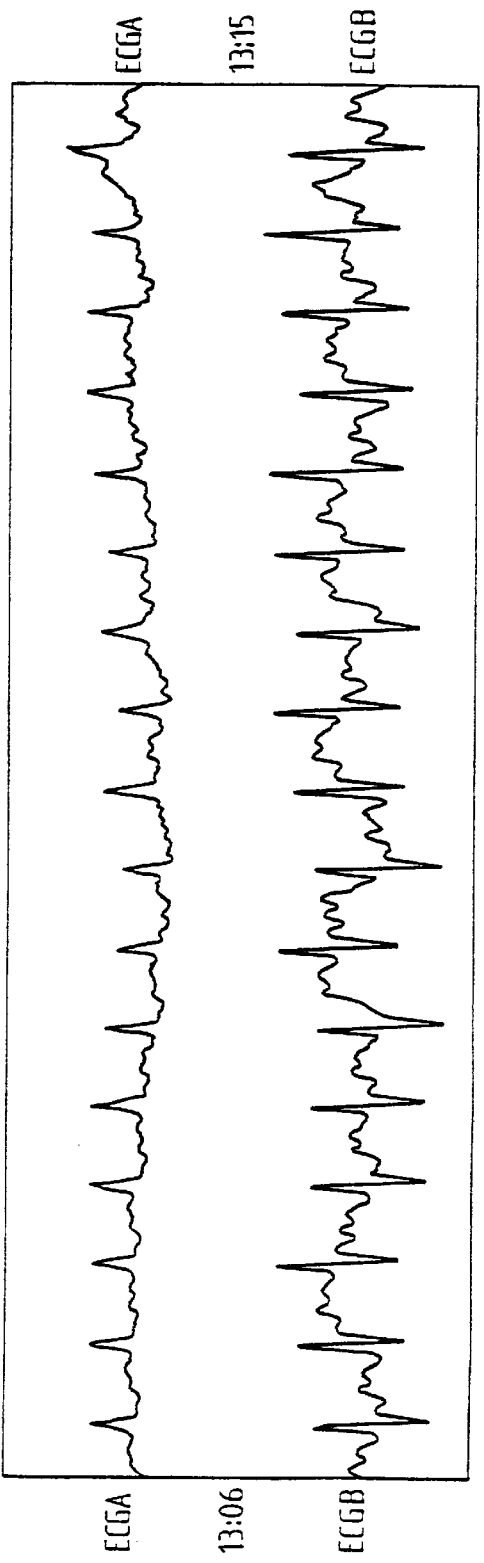
ECG after filtering with FRF without high-pass filter

APPARATUS FOR ENHANCING SIGNALS IN ECGS ARTEFACTS

The present invention relates to an apparatus for enhancing signals in electrocardiograms (ECG) including artefacts. Artefacts occur in electrocardiograms in particular during ergometric testing such as on a bicycle ergometer and treadmill, and when registering long-term ECGS.

Artefacts occurring in ECGs can be subdivided into fixed frequency interferences and random disturbances, the latter in turn into the categories muscle trembling, movement artefacts and base-line wander.

For the removal of fixed frequency interferences such as power-line noise, various methods have become known:

For example, a power frequency compensation filter can be employed (cf JP 1-227 740 A (Abstract)). But it Is also possible to remove fixed frequency interferences under condition that in the signal there are epochs between the QRS complexes and epochs in the QRS complexes and that the frequency and the amplitude do not substantially change during these epochs (of U.S. Pat. No. 5,687,735). Finally base-line wander and power-line noise can be removed also by means of finite-impulse-response (FIR) band-pass filters.

At present random artefacts such as muscle trembling and movement artefacts are reduced by means of low-pass filters such as first-order filters with a cut-off frequency of 20 Hz. Low-pass filters of this type, however, have disadvantageous effects: They reduce in particular the amplitudes in the QRS complex so that these amplitudes cannot be correctly evaluated. But apart from the ST path also the R amplitude is of great significance in particular for judging ischaemiae.

Known methods for removing base-line wander are high-pass filtering on the one hand (of U.S. Periodical: IEEE Transactions on Biomedical Engineering, vol. BME-32, 1985, pp 1052–1060), and the spline method on the other hand (C. R. Meyer and H. N. Keiser: "Electrocardiogram baseline noise estimation and removel using cubic splines and state-space computation techniques", Computers and Biomedical Research, vol. 10, pp 459 to 470, 1977).

A drawback of high-pass filters is the change of the ST path. The measured values of the ST path, e.g. the ST amplitude or the ST slope, are of utmost Importance for the judgment of ischaemiae and the diagnosis of coronary cardiopathy. The spline method causes an undesired delay of the ECG.

Further an apparatus for enhancing the signal-to-noise ratio of ECGs is known (U.S. Pat. No. 5,564,428).

In the known apparatus the signal ensemble is filtered by employing for different segments of the ECG each a filter having a different filter characteristic which is optimum for the respective ECG segment. Correlation and mean value formation are used to determine each the optimum filter coefficients.

Finally there is a method of reducing computations in pattern recognition for an arrhythmical analysis (DE 39 12 028 A1). This method can remove artefacts for quite a specific type of signal processing, namely the arrhythmical analysis. But it is not suited for removing artefacts from ECG curves provided for signal storage and signal reproduction.

For direct judgment of an ECG, an optimally short delay time in the filter unit is aimed at to enable quick recognition of a critical situation of a patient.

It is the object of the present invention to provide an apparatus for enhancing signals in an ECG adapted to reduce the occurrence of random artefacts during signal processing, storage and reproduction to a large extent without inadmissibly distorting the ECG itself or delaying it.

For accomplishing this object, the invention provides an apparatus for enhancing signals in ECGs including artefacts, said apparatus comprising a mean value unit for continuously evaluating from an ECG signal the curve shape of a predetermined number of beats from the beginning of a QRS complex to the end of a T wave and for continuously forming therefrom a mean value beat, a subtracting unit for subtracting the mean value beat from the ECG signal of an actual beat to obtain a residual signal, a filter unit for subjecting the residual signal to high-low pass-filtering and for delaying it to obtain a filtered signal, and an adding unit for adding the mean value beat to the filtered signal.

Thus in the apparatus under the present invention, during an ergometric test, e.g, on a treadmill, a mean value beat is continuously computed by mean value formation of e.g. sixteen preceding well correlating ECG cycles. Of course more cycles or leer cycles may be used as well for evaluation.

The thus obtained mean value beat is then subtracted from an ECG signal of an actual beat and the resulting residual signal is supplied to a filter unit for high-low pass filtering. Subsequently, the mean value beat is again added to the filtered residual signal at the place at which it had been subtracted.

By continuous actualization of the mean value beat, the biologically conditioned change of the QRS character is considered which, for example, can come about by increasing stress during the ergometric test. The mean value beat represents the actual ECG.

Subtraction of the mean value beat from the ECG signal of an actual beat and addition to the filtered residual signal are made in a correct sequence so that the mean value beat obtained e.g. from sixteen ECG cycles is subtracted each in sequence from the actual ECG signal and added to the actual filtered signal. But in doing so, merely the segment from the beginning of the QRS complex to the end of the T wave is used in an ECG cycle. In other words: The p-wave preceding the QRS complex is not considered for subtraction and accordingly not for subsequent addition. The reason therefor is an uncertain association of the P wave with the QRS complex, what applies in particular to supraventricular extrasystols (SES), artrial fibrillation and AV blocks of the second and third degree.

The p-waves thus are not subjected to signal enhancement by the apparatus under the present invention. The p-waves rather can be subjected e.g. to low-pass filtering with 10 Hz. Namely, as in a surface ECG the frequency content of the p-waves is low, the effect of a low-pass filter of 10 Hz on the p-waves can be accepted.

Also on the occurrence of ventricular extrasystols (VES), subtraction of the mean value beat is not made. The VES rather are subjected—similarly to the p-waves—to low-pass filtering with 10 Hz. Namely, as in a surface ECG the frequency content of the VES is reduced, the effect of low-pass filtering with 10 Hz on the VES can be accepted.

The ECG signal can be comprised of one or several derivations. Accordingly, also the mean value beat then is comprised of one or a plurality of derivations.

Also a plurality of different mean value beats can be processed by the apparatus under the present invention. The mean value unit then is capable of forming one or several mean value beats. The subtracting unit selects the best-fitting mean value beat and subtracts it from the actual beat. The adding unit then adds the mean value beat selected by the subtracting unit.

When several different mean value beats are processed, also ventricular extrasystols, the complexes of an intermittent leg block or pace-stimulated QRS complexes can form further mean value beats which are treated in the same way as the first mean value beat.

In Holter systems the ECG can be computed e.g. twice provided the complete ECG is stored in a memory. During the first run, the mean value beats can be formed while during the second run the mean value beats are subtracted from the ECG and added to the filtered residual signal.

As already mentioned above, it could be considered in principle to use conventional low-pass filters for artefact suppression, such as first-order filters with a cut-off frequency of 20 Hz. But low-pass filters of this type have disadvantageous effects: In particular, they reduce the amplitudes in the QRS complex so that these amplitudes cannot be correctly evaluated. But apart from the ST path also the R amplitude is of great significance especially for the judgment of ischaemiae.

For direct judgment of an ECG an optimally short delay time in the filter unit is aimed at. This delay time merely is 1 second in the finite-impulse-response (FIR) filter used as the filter unit.

For accurate operation of the apparatus under the present invention, the correlation of QRS complexes and thus the formation of mean value beats is a precondition. Provided this formation of the mean value beats is not guaranteed, the filter unit will automatically turn off by outputting the unfiltered signal.

For the low-pass filter of the filter unit, preferably a FIR filter is employed which has the following filter equation:

$$y_{n-\frac{N}{2}} = \frac{x_n + x_{n-1} + x_{n-2} + \ldots + x_{n-N+1}}{N} \quad (1)$$

where $X_n, X_{n-1}, \ldots$ is the representation of the input signal, $$y_{n-\frac{N}{2}}$$

is the output signal supplied by the low-pass filter and N depends on the frequency and has e.g. the value 24 for a low-pass filter for 10 Hz.

But depending on the desired filtering effect, also smaller values can be used for N. Useful values for N at a sampling frequency of 500 Hz are within a range of from 6 to 24. That corresponds to cut-off frequencies of about 10 Hz to 40 Hz. Also other sampling frequencies are possible. The delay d of the signal is constant and is satisfied by $$d = \frac{N * T}{2} \quad (2)$$

where T is the sampling interval.

The required computing time is small because the above equation (1) with $$S_{n-1} = x_{n-1} + x_{n-2} + \ldots + x_{n-N+1} + x_{n-N} \quad (3)$$

can be reduced to:

$$y_{n-\frac{N}{2}} = \frac{x_n + S_{n-1} - x_{n-N}}{N} \quad (4)$$

so that merely one addition, one subtraction and one division must be made.

The high-pass filter used for the FIR filter unit is a filter having the following characteristic:

$$y_{n-\frac{N}{2}} = x_{n-\frac{N}{2}} - \frac{x_n + x_{n-1} + x_{n-2} + \ldots + x_{n-N+1}}{N} \quad (5)$$

For this high-pass filter, e.g. N≈500 applies at a sampling frequency of 500 Hz. Depending on the desired filtering effect, also higher values can be used for N. Useful values for N at a sampling frequency of 500 Hz are in the range of from 500 to 5000, corresponding to cut-off frequencies of from about 0.5 Hz to 0.05 Hz.

Also other sampling frequencies are possible.

Also the high-pass filter causes a constant delay d of the signal which similarly to equation (2) is satisfied by the equation:

$$d = \frac{N * T}{2} \quad (6)$$

Also here the required computing time is small because the above equation (5) can be reduced by the equation:

$$S_{n-1} = x_{n-1} + x_{n-2} + \ldots + x_{n-N+1} + x_{n-N} \quad (7)$$

to:

$$y_{n-\frac{N}{2}} = \frac{x_n + S_{n-1} - x_{n-N}}{N} \quad (8)$$

That means that for the computation of the high-pass filter, only one addition, two subtractions and one division must be made.

As a concrete embodiment of the filter unit for a sampling rate of e.g. 500 Hz, a low-pass filter for 10 Hz can have the following filter equation:

$$y_{n-12} = \frac{x_n + x_{n-1} + x_{n-2} + \ldots + x_{n-33}}{24} \quad (9)$$

Accordingly, a high-pass filter for 0.5 Hz and 0.32 seconds, respectively, has the following characteristic;

$$y_{n-250} = x_{n-250} - \frac{x_n + x_{n-1} + x_{n-2} + \ldots + x_{n-408}}{500} \quad (10)$$

The apparatus according to the present invention is capable of processing an electrocardiogram comprised of one or several channels.

Further it is to be noted that the filter unit operates irrespective of the number of derivations.

Now the invention is described in detail in the following with reference to the appended drawings in which:

FIGS. 2 to 10 are ECG diagrams demonstrating which effects mean value (MVB) subtraction, low-pass filtering, high-pass filtering and MVB addition have on the signal representation.

Figure 1:
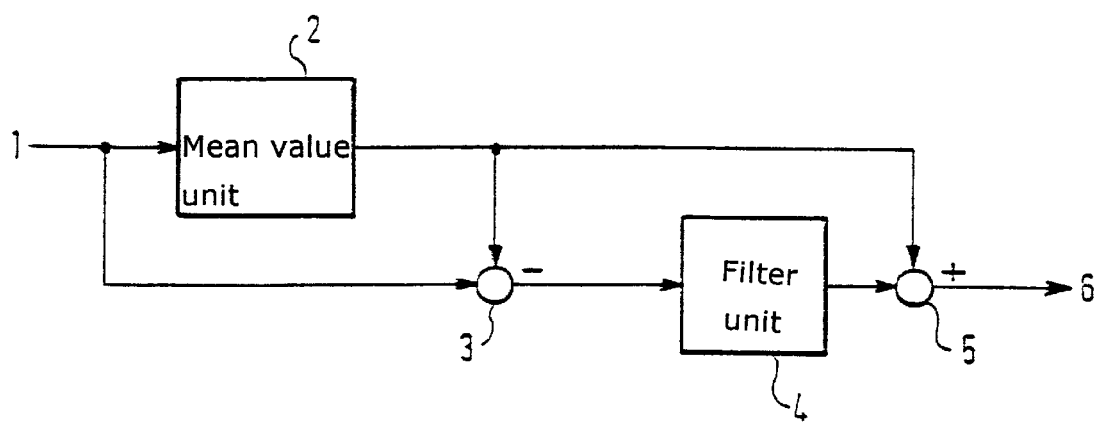
FIG. 1 is a block diagram of the apparatus of the present invention.

An ECG signal is present at an input terminal 1 of the apparatus shown in FIG. 1, which signal is supplied to the mean value unit 2 in which a mean value beat is computed by mean value formation from e.g. 16 well-correlating ECG cycles. This mean value beat is fed to an input terminal of a subtracter 3 at the other input terminal of which the ECG signal is present. The residual signal produced by the subtracter 3 is supplied to a filter unit 4 comprising a FIR high-pass filter and a FIR low-pass filter. After high and low-pass filtering in the filter unit 4, the filtered residual signal is added to the mean value beat in an adder 5 to thereby finally provide the filtered ECG signal at an output 6.

The low-pass filter and the high-pass filter in the filter unit 4 satisfy the filter equations (1) and (5), as explained above.

The delay time in the filter unit 4 only is about 1 second. Solely the use of the FIR filter unit 4 for the ECG signal at the input terminal 1 without the mean value circuit 2 has the effect that the amplitudes of the QRS complex are considerably reduced by the low-Pass filter in the filter unit 4. For this, reason the mean value unit 2 with the aid of which the mean value beat is subtracted before the filter unit 4 and is added behind the filter unit 4 is of special advantage.

The filter unit 4 is composed of digital filters which preferably are realized by software. Concrete dimensionings for this filter unit 4 are given by the above equations (9) and (10) for a sampling rate of 500 Hz. But if desired, also other filters can be employed if they are capable of providing a constant delay.

FIGS. 2 to 10 show each the same section of an ECG signal which was subjected to different processing steps.

Figure 2:
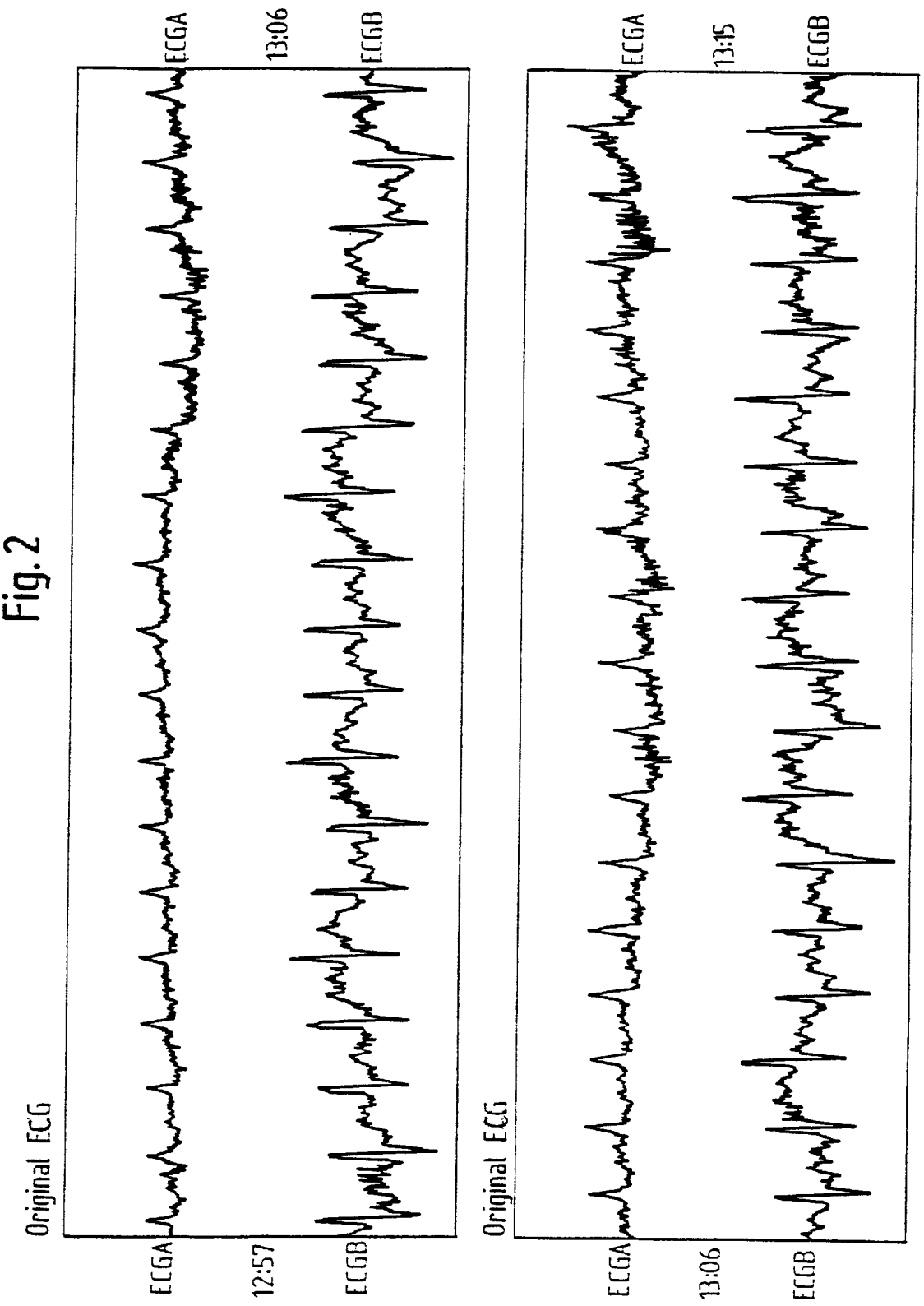

FIG. 2 shows the original ECG wherein noise and base-line wander can be clearly seen, especially in the second channel.

FIG. 3 shows the curve of the ECG signal after treatment by the apparatus of the present invention and in particular after filtering by the FIR filter unit 4: Noise and base-line wander have been filtered out here, as can be clearly seen.

Figure 4:
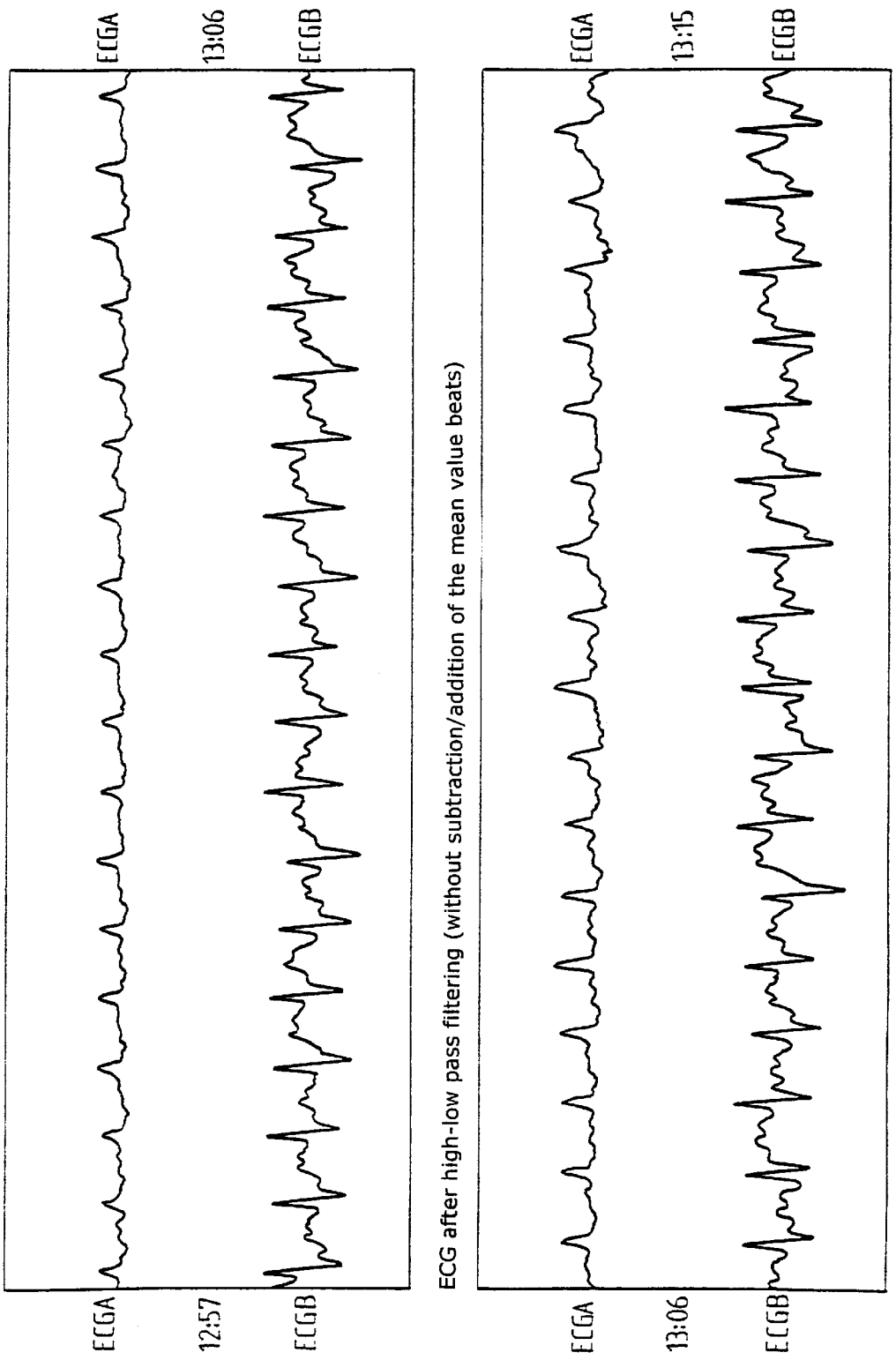

FIG. 4 shows the ECG after high-low-pass filtering, but without subtraction and addition, respectively, of the mean value beat. Here noise and base-fine wander in fact have been filtered out but there clearly are amplitude reductions of the QRS complexes.

FIG. 5 shows a residual signal without high-low-pass filtering. There are no noise and base-line wander.

Figure 6:
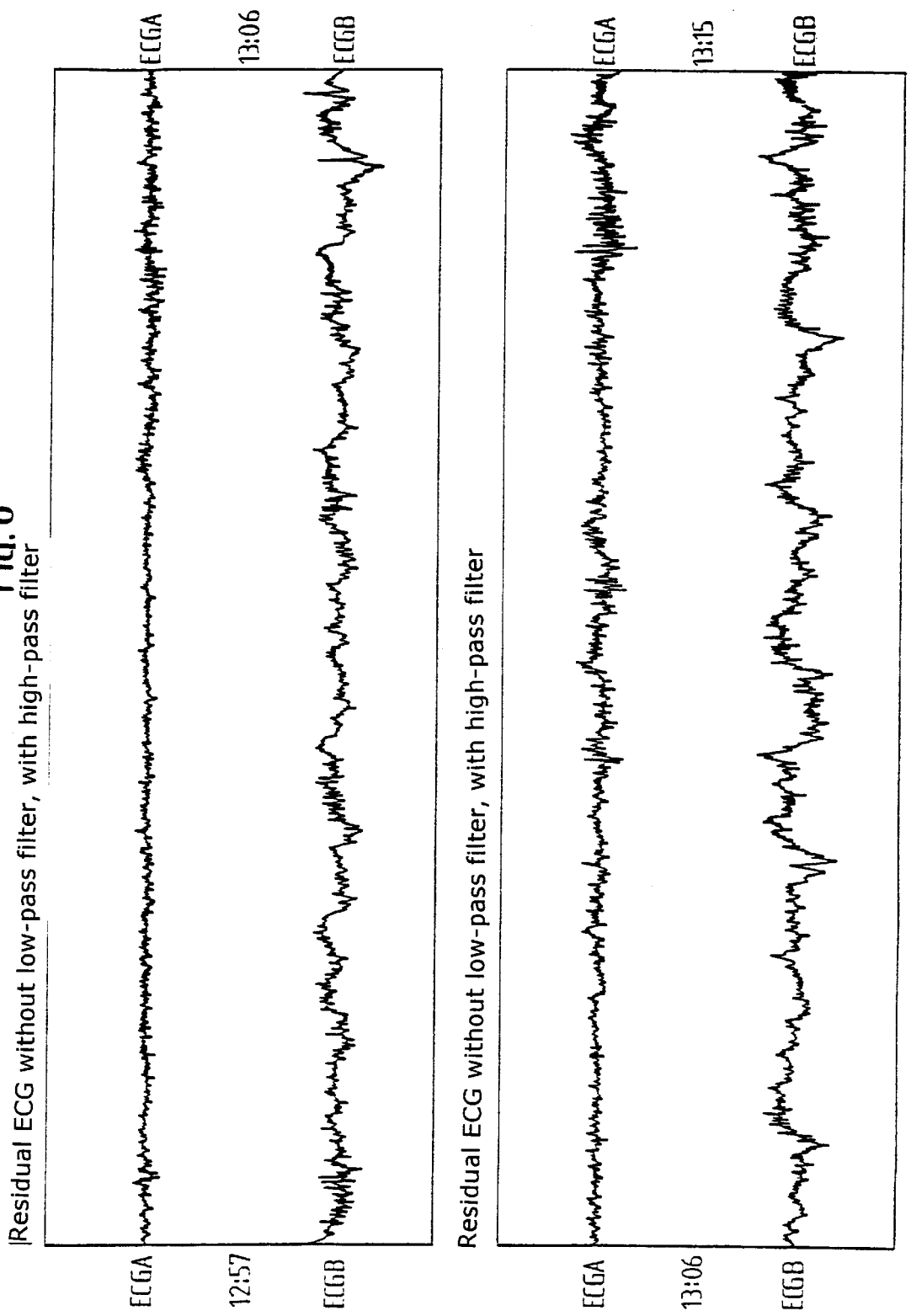

FIG. 6 shows the residual signal without low-pass filtering, but with high-pass filtering. Base-line wander has been removed here, but the noise still is present.

Figure 7:
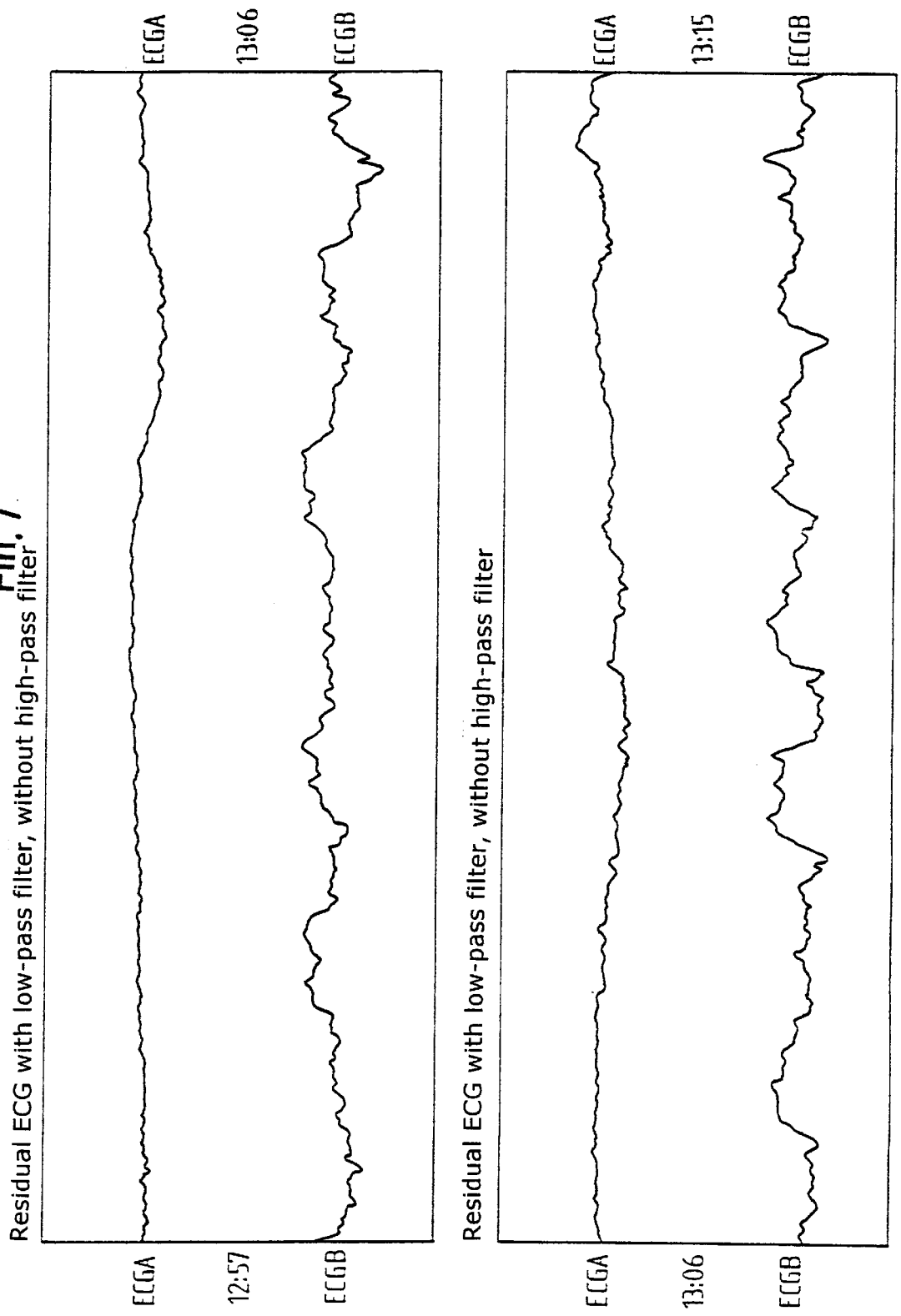

FIG. 7 shows the residual signal with low-pass filtering, but without high-pass filtering. The noise has been removed here, but base-line wander still is present.

FIG. 8 shows the residual signal with high-low-pass filtering. Similarly as in FIG. 3, noise and base-line wander have been filtered out here.

FIG. 9 shows the ECG after filtering by means of a FIR filter unit without low-pass filter. Base-line wander has been removed here, but the noise is still present.

Finally FIG. 10 shows an ECG after filtering by means of an FIR filter unit without high-pass filter. The noise has been removed here, but base-line wander still is present.

The following table shows again schematically which processing steps were made in the respective ECG records of FIGS. 2 to 10.

| FIG. | MVB Subtraction | Low-Pass Filter | High-Pass Filter | MVB Addition |
|---|---|---|---|---|
| 2 | | | | |
| 3 | x | x | x | x |
| 4 | | x | x | |
| 5 | x | | | |
| 6 | x | | x | |
| 7 | x | x | | |
| 8 | x | x | x | |
| 9 | x | | x | x |
| 10 | x | x | | x |

What is claimed is:

1. An apparatus for enhancing signals in electrocardiograms (ECG) including artefacts, said apparatus comprising:

a mean value unit (2) for continuously evaluating from an ECG signal the curve shape of a predetermined number of beats from the beginning of a QRS complex to the end of a T wave and to continuously form therefrom a mean value beat, a subtracting unit (3) for subtracting the mean value beat from the ECG signal of an actual beat to obtain a residual signal, a filter unit (4) for subjecting the residual signal to high-low pass-filtering and for delaying it to obtain a filtered signal, and an adding unit (5) for adding the mean value beat to the filtered signal.

2. The apparatus as set forth in claim 1, characterized in that said subtracting unit (3) subtracts the mean value beat from the ECG signal in the section from the beginning of the QRS complex to the end of the T wave.

3. The apparatus as set forth in claim 1 characterized in that said filter unit (4) is a finite-impulse response (FIR) filter.

4. The apparatus as set forth in claim 1 characterized in that the delay time of said filter unit (4) is constant.

5. The apparatus as set forth in claim 1 characterized in that the delay time of said filter unit (4) is about 15.

6. The apparatus as set forth in claim 3, characterized in that said filter unit (4) comprises a low-pass filter with the following filter equation:

$$y_{n-\frac{N}{2}} = \frac{x_n + x_{n-1} + x_{n-2} + \ldots + x_{n-N+1}}{N}$$

where

N=24 at a sampling rate of 500 Hz, x=input signal, y=output signal.

7. The apparatus as set forth in claim 2 characterized in that said filter unit (4) includes a high-pass filter with the following filter equation:

$$y_{n-\frac{N}{2}} = x_{n-\frac{N}{2}} - \frac{x_n + x_{n-1} + x_{n-2} + \ldots + x_{n-N+1}}{N}$$

where

N=500 at a sampling rate of 500 Hz, x=input signal, y=output signal.

8. The apparatus as set forth in claim 3, characterized in that said filter unit (4) includes a low-pass filter with the following filter equation:

$$y_{n-\frac{N}{2}} = \frac{x_n + x_{n-1} + x_{n-2} + \ldots + x_{n-N+1}}{N}$$

where $$N = M * \frac{\text{sampling rate [Hz]}}{500\,\text{Hz}}$$

with $6 \leq M \leq 24$ x=input signal, y=output signal.

9. The apparatus as set forth in claim 2 characterized in that said filter unit (4) includes a high-pass filter with the following filter equation:

$$y_{n-\frac{N}{2}} = x_{n-\frac{N}{2}} - \frac{x_n + x_{n-1} + x_{n-2} + \ldots + x_{n-N+1}}{N}$$

where $$N = M * \frac{\text{sampling rate [Hz]}}{500\,\text{Hz}}$$

with $500 \leq M \leq 5000$ x=input signal, y=output signal.

10. The apparatus as set forth in claim 1 characterized in that an electrocardiogram comprised of one or a plurality of channels can be processed.

11. The apparatus as set forth in claim 1, characterized in that said mean value unit (2) is capable of supplying several different mean value beats, said subtracting unit (3) selects the best-fitting mean value beat and subtracts it from the ECG signal of the actual beat, and said adding unit (5) adds the mean beat value selected by said subtracting unit (3) to the filtered signal.

* * * * *